United States Patent
Gamelin

(10) Patent No.: US 10,039,878 B2
(45) Date of Patent: Aug. 7, 2018

(54) METHOD FOR RELIABLE INTERMODULE CONNECTION IN AN INFUSION SYSTEM

(71) Applicant: CareFusion 303, Inc., San Diego, CA (US)

(72) Inventor: Andre Gamelin, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 1140 days.

(21) Appl. No.: 13/889,219

(22) Filed: May 7, 2013

(65) Prior Publication Data

US 2014/0336576 A1    Nov. 13, 2014

(51) Int. Cl.
 *A61M 5/142* (2006.01)
 *G01R 31/02* (2006.01)
 *G01R 19/00* (2006.01)
 *A61M 5/14* (2006.01)
 *A61M 5/168* (2006.01)

(52) U.S. Cl.
 CPC ........... *A61M 5/142* (2013.01); *G01R 31/024* (2013.01); *A61M 5/1407* (2013.01); *A61M 5/14228* (2013.01); *A61M 5/16827* (2013.01); *A61M 2205/27* (2013.01); *A61M 2205/6018* (2013.01); *A61M 2205/702* (2013.01); *G01R 19/0038* (2013.01)

(58) Field of Classification Search
 CPC .... A61M 5/172; A61M 5/142; G01R 19/0092
 USPC ................................. 324/538–544
 See application file for complete search history.

(56) References Cited

U.S. PATENT DOCUMENTS

| | | | | |
|---|---|---|---|---|
| 3,978,465 A | * | 8/1976 | Goode .................... | G01R 27/18 324/510 |
| 7,518,529 B2 | * | 4/2009 | O'Sullivan .......... | G01R 15/142 324/126 |
| 8,294,474 B2 | * | 10/2012 | Ahrens .................... | H04L 25/08 324/522 |
| 8,686,738 B2 | * | 4/2014 | Sexton ..................... | H02H 3/10 324/539 |
| 2011/0012613 A1 | * | 1/2011 | Gong .................... | G01R 31/307 324/543 |
| 2011/0158823 A1 | * | 6/2011 | Wang ................ | A61M 5/14228 417/53 |
| 2011/0190694 A1 | * | 8/2011 | Lanier, Jr. ......... | A61M 5/14216 604/67 |
| 2012/0126822 A1 | * | 5/2012 | Panozzo ............... | G01R 31/021 324/543 |
| 2014/0271233 A1 | * | 9/2014 | Calhoun ................. | F04B 23/04 417/44.2 |

* cited by examiner

*Primary Examiner* — Jeff Natalini
(74) *Attorney, Agent, or Firm* — Mintz Levin Cohn Ferris Glovsky and Popeo, P.C.

(57) ABSTRACT

A patient care system is configured for infusing fluid to a patient. The system includes a plurality of modular fluid infusion pumps that each has a connector for connecting to a modular programming unit or to one another. Systems and methods are configured for verifying that the connectors are reliably performing their functions or communicatively connecting the pumps to one another or to the programming unit.

8 Claims, 5 Drawing Sheets

METHOD FOR RELIABLE INTERMODULE CONNECTION IN AN INFUSION SYSTEM

BACKGROUND

A hospital patient often has the need for multiple intravenous (IV) infusions from multiple supplies of fluids, such as drugs. This requires the use of multiple infusion pumps that are connected to the patient and to fluid containers via fluid lines. There exist modular infusion systems in which pump and monitoring modules can be selectively attached, both physically and electrically, to a central programming unit or to one another via one or more connectors. The central programming unit controls the operation of pump modules attached to it, and receives and displays information regarding the pump modules.

The connectors that are used to attach the modules to the central programming unit are typically formed of one or more materials that have good electrical conductivity. For example, the connectors may be formed of a base metal of high conductivity (such as copper) that is coated with a metal that provides protection from oxidation (i.e. such as gold).

The connectors include contact elements that are exposed to the environment. The environmental exposure makes the contact elements susceptible to damage or wear from environmental elements such as cleaners, contaminants, chemicals, fluids, and particulates. The connector may also become physically damaged due to normal, mechanical attachment and detachment of the modules. Moreover, as the connectors wear, the metal coating may remove over time resulting in undesirable exposure of the base metal to the environment.

Such damage and wear to the connectors may lead to a loss of electrical connectivity or unintended connectivity between connectors. This may have negative implications for the patient. There is therefore a need for systems and methods for verifying the reliability of the connector in a modular infusion system.

Another common practice is to use circuit breakers on lines to protect against short circuits. While this practice can protect against high current short circuits, it can't protect against current shorts that are higher impedance since the circuit protection must be set at a current that is higher than the maximum possible current over all operating conditions. It is also common practice to provide redundant contacts, however a system with redundant contacts alone would not be able to detect if the redundant contacts have been compromised. After a period of time, the last redundant contact might fail leading to negative implications for the patient. Creating a system that can be switched and tested offline may help to detect failed contacts, but would require that the circuit be disrupted in order to test which may only be feasible upon power up. There is therefore a need for systems and methods for verifying the integrity of connector contacts without disrupting the use of the circuit.

SUMMARY

A patient care system is configured for infusing fluid to a patient. The system includes a plurality of modular fluid infusion pumps that each has a connector for connecting to a modular programming unit and/or to one another. Disclosed herein are systems and methods for verifying that the connectors are reliably performing their functions or communicatively connecting the pumps to one another or to the programming unit.

In one aspect, there is disclosed a method for verifying reliability of a plurality of connector contacts between a first modular pump device and a second modular pump device, the method comprising: obtaining a measurement for each of a plurality of contacts associated with a powered line; comparing the measurements from each contact of a powered line; and determining whether to affect the operation of the first and second pump devices based on the comparison.

In another aspect, there is disclosed a patient care system for infusing multiple medical fluids, the patient care system comprising: a plurality of fluid containers each adapted to hold a separate medical fluid; a plurality of fluid lines each in fluid communication with a separate fluid container from among the plurality of fluid containers; a plurality of modular pump devices connected to one another via at least one connection, each pump adapted to receive and connect to a separate fluid line from among the plurality of fluid lines and to operate on the received conduit to pump the fluid from the fluid container connected to the received conduit; a plurality of electrical current sensors configured to sense electrical currents in power lines and ground lines that pass through the connector; and a processor connected to the plurality of current sensors and to the plurality of modular pump channels, the processor configured to sense an electrical current in at least two power lines that connect a first modular pump device and a second modular pump device; sense an electrical current in at least two ground lines that connect the first modular pump device and the second modular pump device; compare the sensed currents; and determine whether to affect the operation of the first and second pump devices based on the comparison.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

A patient care system is configured for infusing fluid to a patient. The system includes a plurality of modular fluid infusion pumps that each has a connector for connecting to a modular programming unit and/or to one another. Disclosed herein are systems and methods for verifying that the connectors are reliably performing their functions or communicatively connecting the pumps to one another or to the programming unit.

As described in detail below, the connector includes a connector interface having one or more interconnections elements each associated with a connection. A method to measure the state of each interconnection element is also disclosed. In this regard, based on information obtained about an interconnection element, a decision matrix is applied to determine actions or inactions related to the state of the interconnection element.

An example modular infusion pump system is first described with reference to FIG. 1, which shows a patient care system 20 having four infusion pumps 22, 24, 26, and 28. A programming module 60 is attached to infusion pumps 26 and 24. In this regard, each of the infusion pumps 22, 24, 26, and 28, as well as the programming module 60, includes at least one connector element configured to mechanically and communicatively connect to a connector element of another infusion pump or programming module. The mechanical element may be any type of mechanical connection that is configured to connect a modular infusion pump to another modular infusion pump or programming module.

It should be appreciated that the relative positions and orientation of the pumps relative to one another and to the programming module may vary.

Figure 1:
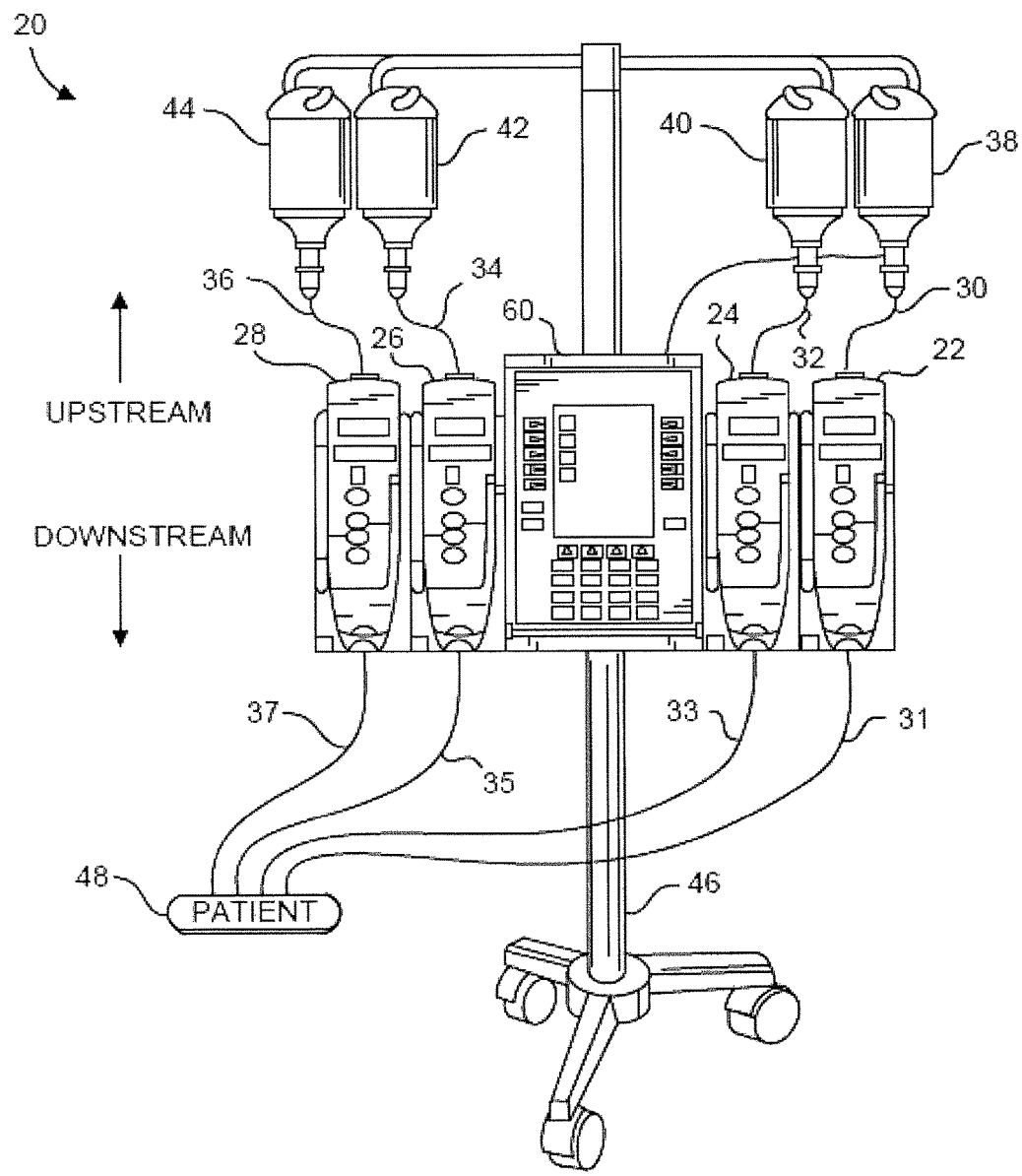
FIG. 1 is a front view of a patient care system having four modular fluid infusion pumps, each of which is connected to a respective fluid supply for pumping the contents of the fluid supply to a patient.

With reference still to FIG. 1, each of the infusion pumps 22, 24, 26, and 28 is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as tubing, through which fluid can flow through. Fluid supplies 38, 40, 42, and 44, which may take various forms but in this case are shown as bottles, are inverted and suspended above the pumps. Fluid supplies may also take the form of bags or other types of containers. Both the patient care system 20 and the fluid supplies 38, 40, 42, and 44 are mounted to a roller stand or IV pole 46.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other. Typically, inter-module connections are used continuously during operation for power and communications. The integrity of these connections can be critical to ensure that infusions are not interrupted.

Typically, medical fluid administration sets have more parts than are shown in FIG. 1. Many have check valves, drip chambers, valved ports, connectors, and other devices well known to those skilled in the art. These other devices have not been included in the drawings so as to preserve clarity of illustration.

It should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater. There would be more of an opportunity for the upstream fluid lines 30, 32, 34, and 36 to become intertwined with each other when all four are dangling from the bottles, which can cause confusion as to which tube should be in which infusion module. The opportunity for confusion increases as the number of tubes increases.

Figure 2:
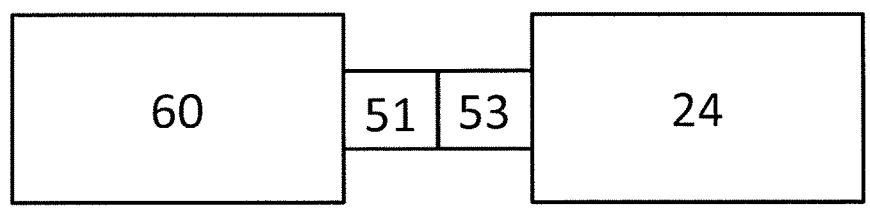
FIG. 2 shows a schematic representation of two modular pumping units, including an example modular pump attached to a modular programming module.

FIG. 2 shows a schematic representation of an example modular infusion pump 24 attached to the programming module 60. The programming module 60 includes a connector element 51 that removably attaches to a connector element 53 of the modular infusion pump 24. The connector elements 51 and 53 may be any type of connector that is configured to connect to one another for transmission of electrical and/or communication signals. The connector elements may be, for example, male and female type connector elements made of any of a variety of materials that may include a base material and a coating. The infusion pump 24 may have one or more connector elements configured to connect to a connector element of one of the other infusion pumps 22, 26, and 28.

One or both of the infusion pump 24 and the programming unit 60 may include microprocessor, computer memory and software configured to perform a method for verifying a state of the connection between the connection elements 51 and 53. This enables a modular pump connector element with enhanced reliability for critical applications.

Figure 3:
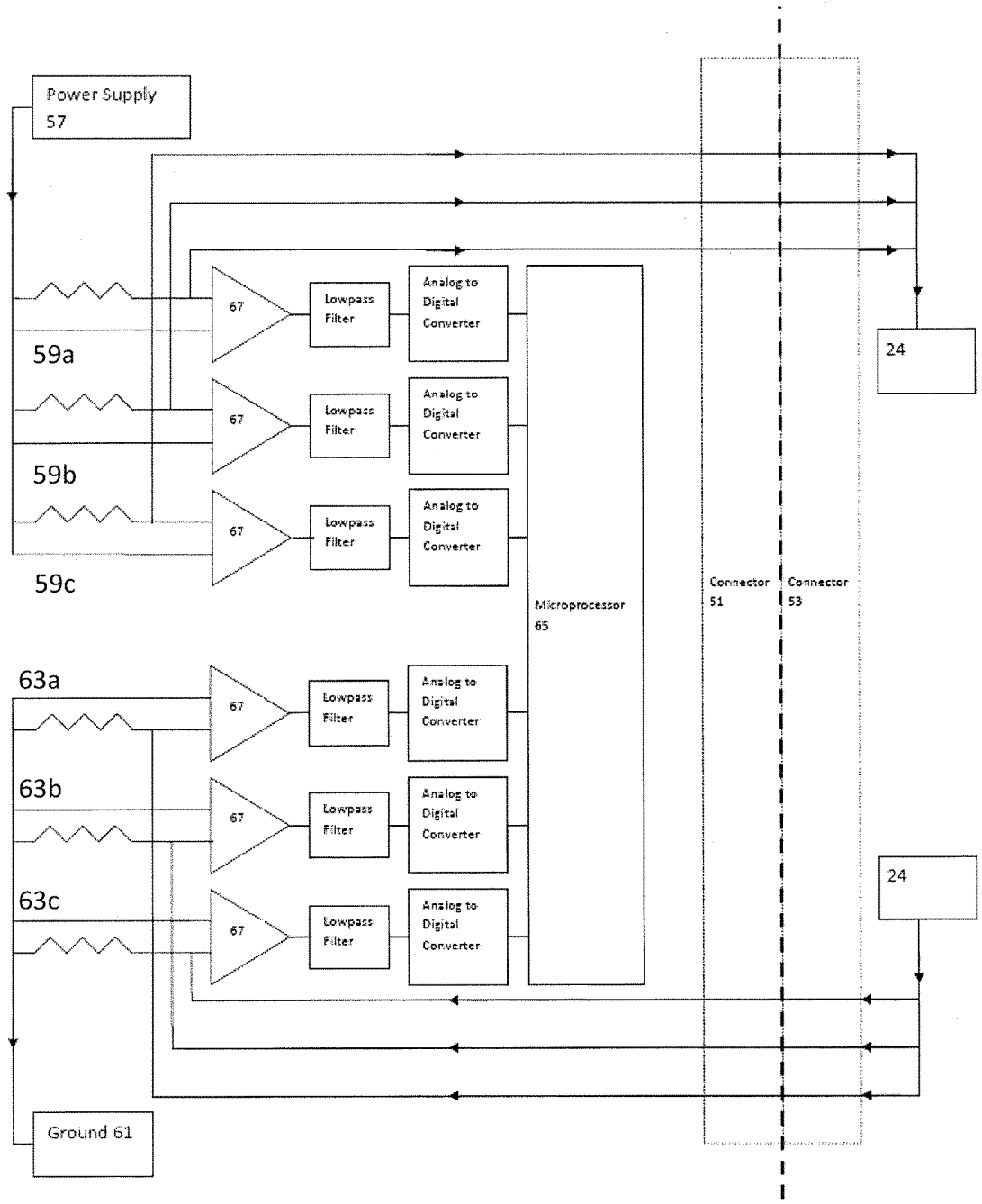
FIG. 3 shows a schematic circuit diagram of a connector interface for a pair of connector elements for modular units of the infusion system.

FIG. 3 shows a schematic circuit diagram of a connector interface for a pair of connector elements 51 and 53 of the infusion system. The diagram shows the connector elements 51 and 53, which can be associated with any of the infusion pumps 22, 24, 26, 28 or the programming unit 60. For purposes of this description, the connector elements 51 and 53 are described as being associated with the pump 24 and programming unit 60, respectively.

With reference to FIG. 3, a power supply 57 is connected to one or more power lines 59*a*, 59*b*, and 59*c* of the programming unit 60. Likewise, a ground 61 is connected to one or more ground lines 63*a*, 63*b*, and 63*c* of the programming unit 60. Each of the power and ground lines communicates with a microprocessor via a respective sensor 67 configured to sense electrical current in the line. Any of a variety of components, such as a filter and an analog to digital converter may be supplied as shown in FIG. 3. In addition, the power and ground lines are coupled to the connector elements 51 and 53 as well as to a power module 71 and a return or feedback module 73 of the infusion pump 24.

The microprocessor 65 is configured to monitor and report the status of the connector elements by analyzing the state of the current through one or more of the power lines 59 and ground lines 61. The microprocessor may compare current between contacts with the same signal type. For example, lines 59*a, b*, and *c* are compared against each other and an expected range. In this regard, the microprocessor 65 may have access to a decision matrix that is applied to determine actions taken based on the sensed currents. The microprocessor 65 may be programmed with the decision matrix or it may access software programmed to achieve the decision matrix.

According to a first embodiment, the decision matrix is configured to consider criteria prior to the programming module 60 or the infusion pump 24 starting a critical task, such as pumping fluid into a patient. Based on the criteria, the microprocessor may trigger one or more actions, such as alerting a user to a condition or requesting action from the user (such as re-connecting the module), or inhibiting operation of the pump module(s). A first such criteria includes determining, based on input received from the current sensors 67, whether at least two power lines 59 and two ground lines 63 have the same current measurement. This is an indication of redundancy in the power lines and the ground lines, which is at least one indication of a safe operating condition. If the first criteria is satisfied, then the microprocessor does not inhibit operation of the modules. The microprocessor may optionally send out a signal to the user that the redundancy criteria is satisfied.

A second criteria includes determining whether any short circuits are present in the connector elements. The presence of a high current measurement in any of the power or ground lines may be an indication of a short circuit being present. Another criteria includes determining whether an open circuit is present in the connector elements, which would be indicated by the presence of a low current in any of the power or ground lines. If a short circuit or open circuit is deemed present, the microprocessor inhibits operation of the modules and/or sends a signal to a user that a short circuit or open circuit has been detected. The microprocessor may qualify the presence of a short circuit or open circuit based on a prolonged duration of the high or low current or based upon a repeated quantity of measurements. In an embodiment, a high current on a single contact would be significantly higher than the other contacts. A short circuit would be where all contacts are higher than the maximum expected current draw for the module. An open circuit on a single contact would be significantly lower than the other contacts (close to zero current). An open circuit elsewhere would result in all contacts close to zero current.

After the criteria for starting a critical task has been satisfied and during operation of the infusion pump, the microprocessor may continue to monitor status of the connections. Based on the monitored status, the microprocessor may take certain actions, such as to warn or notify the user that a maintenance action should be taken immediately or should be taken within a predetermined time period. The microprocessor may also instruct a user to disconnect and reconnect one modular pump to another modular pump such as to wipe the connections. For example, if an open circuit or short circuit condition is detected during operation of a modular pump unit, the microprocessor may take such action. Or the microprocessor may detect a power condition such as lack of power or ground redundancy. This permits the user to take the action within an appropriate time period. In the case of a short circuit being detected on a power or ground line, the microprocessor may trigger a switch that causes a shut off the line where the short circuit is present.

It should be appreciated that the microprocessor may be configured with various decision matrices configured to act on various conditions in the connector elements beside power conditions. For example, the microprocessor may be connected to one or more sensors that sense data being transferred across data lines in the connector elements. The microprocessor may verify redundant communication lines, for example, by comparing sensed data being transferred across the communication lines.

Exemplary Configuration of Modules

Figure 4:
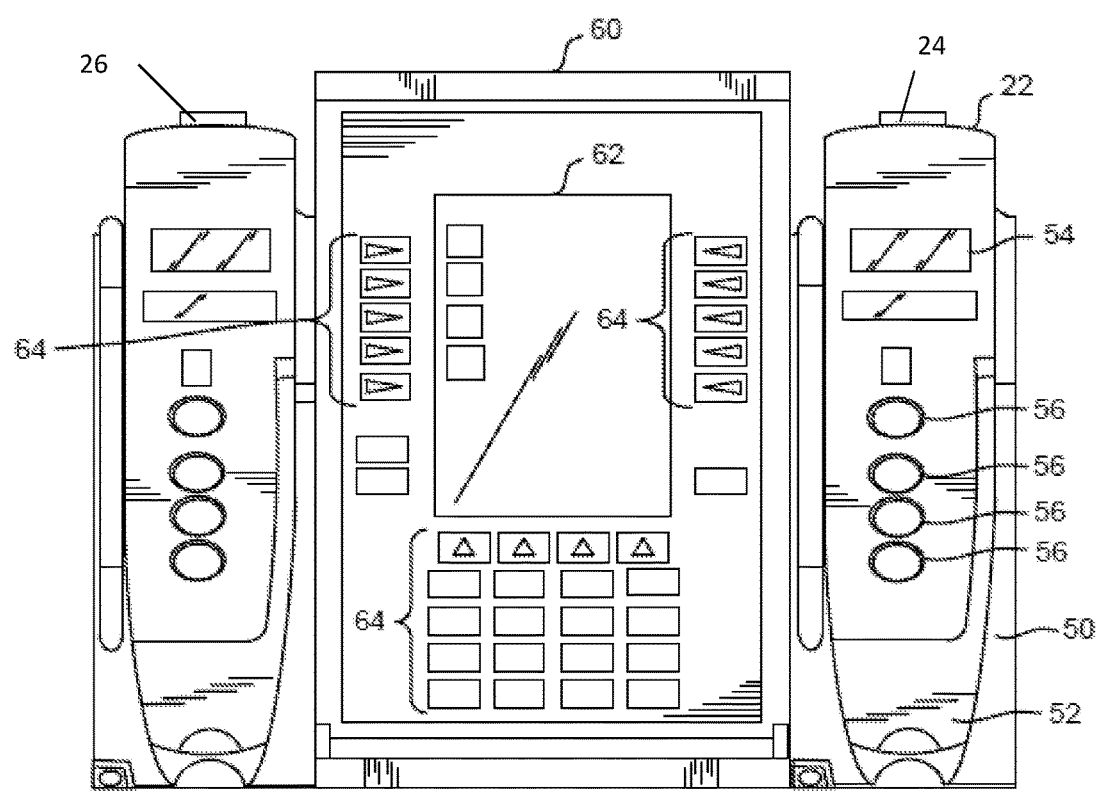
FIG. 4 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 4, an enlarged view of the front of the infusion pumps 24 is shown attached to the programming module 60. The pump includes a front door 50 and a handle 52 that operates to lock the door in a closed position for operation and to unlock and open the door for access to the internal pumping and sensing mechanisms and to load administration pump sets or pump cassettes for the pump. When the door is open, a tube of the pump set can be connected with the pump, as will be shown in FIG. 3. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the infusion pump as desired. The infusion pump 24 also includes audio alarm equipment in the form of a speaker.

Other devices or modules, including another infusion pump, may be attached to the right side of the infusion pump 24, as shown in FIG. 1. In such a system, each attached pump represents a pump channel of the overall patient care system 20. In one embodiment, the programming module is used to provide an interface between the infusion pump 24 and external devices as well as to provide most of the operator interface for the infusion pump 24.

With reference still to FIG. 4, the programming module 60 includes a display 62 for visually communicating various information, such as the operating parameters of the pump 24 and alert indications and alarm messages. The programming module 60 may also include a speaker to provide audible alarms. The programming module also has various input devices in this embodiment, including control keys 64 and a bar code scanner (not shown) for scanning information relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump.

The communications system may take the form of a radio frequency ("RF") (radio frequency) system, an optical system such as infrared, a Blue Tooth system, or other wired or wireless system. The bar code scanner and communications system may alternatively be included integrally with the infusion pump 24, such as in cases where a programming module is not used, or in addition to one with the programming module. Further, information input devices need not be hard-wired to medical instruments, information may be transferred through a wireless connection as well.

FIG. 4 shows a second pump module 26 connected to the programming module 60. As shown in FIG. 1, more pump modules may be connected. Additionally, other types of modules may be connected to the pump modules or to the programming module.

Figure 5:
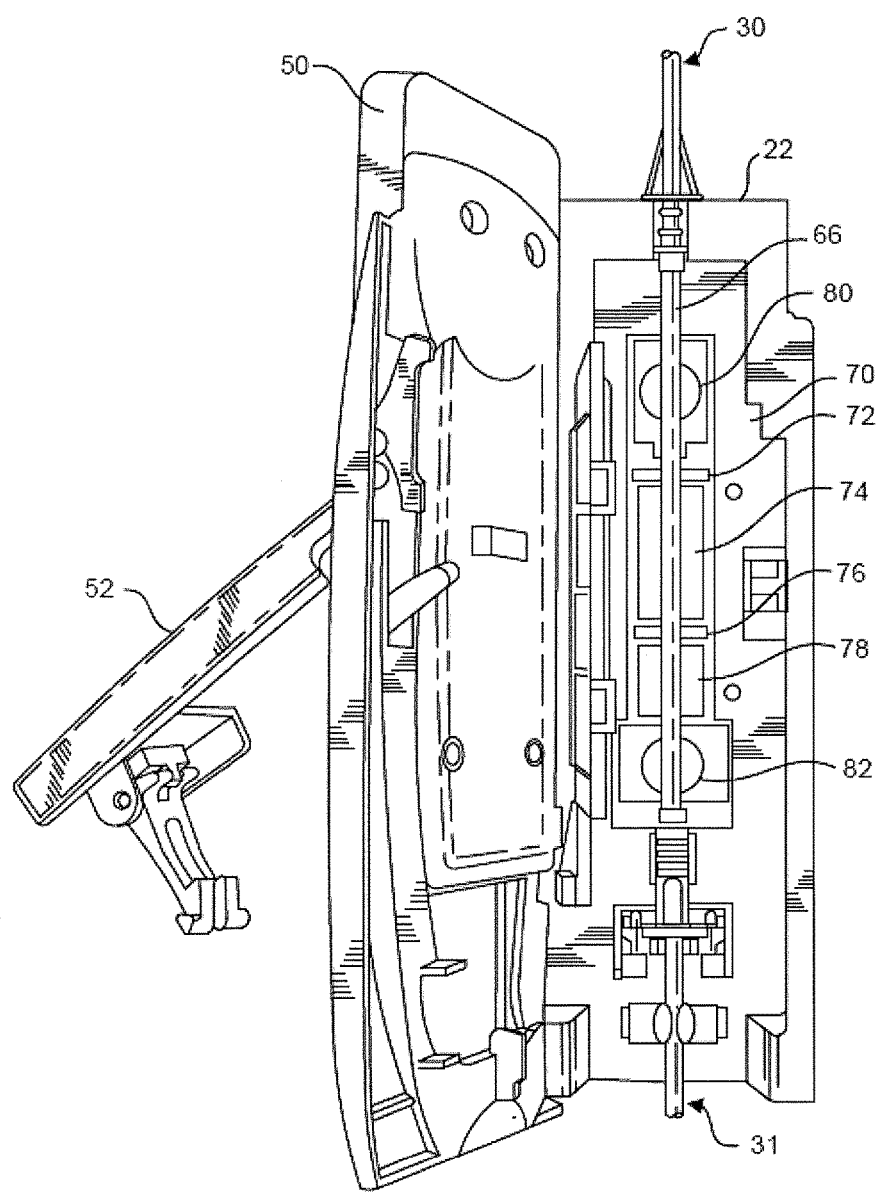
FIG. 5 is a perspective view of one of the fluid infusion with its front door in the open.

Turning now to FIG. 5, an infusion pump 22 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 5 further shows a downstream pressure sensor 82 included in the pump 22 embodiment at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 1) and the flow control device, so that the connection of the correct fluid supply with the correct pump may be verified before any fluid is pumped to the patient.

With reference still to FIG. 5, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A method for verifying reliability of a plurality of connector contacts of a program module that controls and removably connects to a first modular pump device and a second modular pump device via the plurality of connector contacts, the method comprising:

repeatedly obtaining an electrical current measurement for each of a plurality of connector contacts of the program module over a prolonged period of time, the connector contacts associated with at least one powered line, wherein the connector contacts include a first connector contact that connects the program module to the first modular pump device and a second connector contact that connects the program module to the second modular pump device, and wherein the first connector contact transmits an electrical signal or communication signal between the first modular pump device and the program module, and wherein the second connector contact transmits an electrical signal or communication signal between the second modular pump device and the program module;

comparing a first plurality of obtained electrical current measurements of at least the first connector contact with a second plurality of obtained electrical current measurements of at least the second connector contact;

determining that the first plurality of obtained electrical current measurements is higher than the second plurality of obtained electrical current measurements over the prolonged period of time; and notifying a user, based on the determination, that a short circuit is deemed present in at least one of the connector contacts;

and wherein a microprocessor of the program module performs the obtaining, comparing and determining steps.

2. The method of claim 1, wherein at least one of the connector contacts includes the at least one powered line that includes a power supply line, power ground line, or analog signal line.

3. The method of claim 1, wherein at least one of the connector contacts includes the powered line that includes a data or digital signal line and wherein obtaining a measurement comprises collecting data from the powered line.

4. The method of claim 1, further comprising inhibiting operation of the pump devices if one or more of the currents are not the same.

5. The method of claim 1, further comprising sending a warning to a user if one or more currents are not the same.

6. The method of claim 1, further comprising sending a warning to a user if all measured currents exceed a threshold.

7. The method of claim 1, further comprising sending a warning to a user if all measured currents are below a threshold.

8. The method of claim 1, further comprising requesting a user to disconnect and reconnect the program module from one of the first modular pump and the second modular pump.

* * * * *